United States Patent
Fujita et al.

(10) Patent No.: US 7,263,733 B2
(45) Date of Patent: Sep. 4, 2007

(54) BED APPARATUS FOR IMAGE DIAGNOSIS AND ITS ATTACHMENTS

(75) Inventors: Hidehiro Fujita, Tochigi-ken (JP); Takafumi Oguri, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/283,297

(22) Filed: Oct. 30, 2002

(65) Prior Publication Data

US 2003/0084512 A1    May 8, 2003

(30) Foreign Application Priority Data

Oct. 30, 2001    (JP)    ............................ P2001-332302

(51) Int. Cl.
*A61G 13/12* (2006.01)
(52) U.S. Cl. ........................ 5/601; 5/622; 5/623; 5/621
(58) Field of Classification Search ................... 5/601, 5/621, 622–624
See application file for complete search history.

(56) References Cited

U.S. PATENT DOCUMENTS

| | | | | |
|---|---|---|---|---|
| 2,872,259 A | * | 2/1959 | Thorpe | ............................ 5/613 |
| 4,222,136 A | * | 9/1980 | Valentino | ..................... 5/507.1 |
| 4,568,071 A | * | 2/1986 | Rice | ............................... 5/601 |
| 4,698,837 A | * | 10/1987 | Van Steenburg | ............ 378/208 |
| 5,133,097 A | * | 7/1992 | Pyles | ............................. 5/623 |
| 5,353,809 A | * | 10/1994 | Faucher | ......................... 5/646 |
| 5,661,859 A | * | 9/1997 | Schaefer | ........................ 5/621 |
| 6,199,233 B1 | * | 3/2001 | Kantrowitz et al. | ........... 5/601 |

FOREIGN PATENT DOCUMENTS

JP    8-94759    4/1996

* cited by examiner

*Primary Examiner*—Patricia Engle
*Assistant Examiner*—Fredrick Conley
(74) *Attorney, Agent, or Firm*—Oblon, Spivak, McClelland, Maier & Neustadt, P.C.

(57) ABSTRACT

A headrest, armrest, or other attachment to an image diagnosis bed apparatus having leaf springs formed as integral parts of its connecting portion, and a bed apparatus tabletop with a connecting hole for the insertion of the attachment connecting portion at one end and fixing holes for the leaf springs at its top. Also, an armrest shaped so as to be capable of being placed over a headrest connected to the tabletop.

8 Claims, 13 Drawing Sheets

BED APPARATUS FOR IMAGE DIAGNOSIS AND ITS ATTACHMENTS

CROSS-REFERENCE TO RELATED APPLICATIONS

This application claims the benefit of priority to Japanese Patent No. P2001-332302, filed on Oct. 30, 2001, the entire contents of which are incorporated herein by reference.

BACKGROUND OF THE INVENTION

1. Field of the Invention

This invention relates to a bed apparatus used in support of image diagnosis, such as X-ray CT.

2. Description of the Related Art

A bed apparatus used with an image diagnosis apparatus, such as X-ray CT, is generally composed of a tabletop 10 on which a patient (person to be examined) may lie, and a bed 20 that is a base for supporting the tabletop 10 and a device for driving it, as shown in FIG. 1. The tabletop 10 may be fitted with attachments, such as a headrest and an armrest (as shown by dotted lines in FIG. 1). The tabletop 10 is constructed to be horizontally and reciprocally movable along the axis of the body of the person to be examined (along the arrow Z shown in FIG. 1) by a driving device installed in the bed 20.

The tabletop 10 is also constructed so that it can be fitted at its end facing the photographing apparatus with attachments, such as a headrest for supporting the head of the person to be examined and an armrest for supporting his arms. The attachments, such as the headrest and armrest, are fitted in various places, depending on the photographing method that is employed. Arrangements employed in the related art for fitting such attachments are shown by way of example in FIGS. 2 to 4. At its end facing the photographing apparatus, the tabletop 10 has a connecting hole 10a through which the attachments, such as the headrest and armrest, may be connected. At its top, the tabletop 10 has metallic fixing pins 10b for fixing the attachments to the tabletop 10, flexible straps 10c for connecting the fixing pins 10b to the tabletop 10 and fixing holes 10d in which the fixing pins 10b can be inserted for fixing the attachments.

As shown in FIG. 2, the headrest is a supporting device of small thickness for supporting the head of the person to be examined so that it's photographing may be carried out satisfactorily. The headrest 30 can be connected with the tabletop 10 if its connecting portion 30a is inserted into the connecting hole 10a of the tabletop 10. The headrest 30 has fixing holes 30b in its connecting portion 30a, so that if the metallic fixing pins 10b connected to the top of the tabletop 10 by the straps 10c are inserted in its fixing holes 10d provided on the top of the tabletop 10 after the headrest is connected with the tabletop 10, the fixing pins 10b may pass through the fixing holes 30b to fix the headrest to the tabletop 10.

The armrest is used to support the upper arm portions of the person to be examined in the vicinity of his head so that his arms do not obstruct the photographing of the upper half of his body. FIG. 3 is a partly cutaway view of a conventional armrest. The armrest 40 can be connected with the tabletop 10 if its connecting portion 40a is inserted into the connecting hole 10a of the tabletop 10. The armrest 40 has fixing holes 40b in its connecting portion 40a, so that if the fixing pins 10b connected to the top of the tabletop 10 by the straps 10c are inserted in its fixing holes 10d provided on the top of the tabletop 10 after the connecting portion 40a is connected with the tabletop 10, the fixing pins 10b may pass through the fixing holes 40b to fix the armrest to the tabletop 10.

Conventional attachments, however, have a variety of problems as will now be explained. The series of operations associated with connecting and fixing an attachment, such as headrest 30 or armrest 40, to the tabletop 10 are troublesome, since they consist of two steps: (a) inserting the connecting portion of the attachment into the connecting hole 10a of the tabletop 10; and then (b) inserting the fixing pins 10b situated above the tabletop 10 into the fixing holes 10d in the top of the tabletop 10. The conventional armrest 40 is constructed so that its connection to the tabletop 10 is possible only after the removal of the headrest 30. The process of removal and fitting is troublesome. Moreover, the presence of two fixing pins 10b in the conventional system makes it difficult for one person to complete the removal process, since it is necessary to draw out the attachment while drawing up the two pins.

Another drawback of the conventional system relates to differences in the effective range of photographing between when the armrest 40 is used, and when the headrest 30 is used, as shown in FIGS. 4A and 4B. When the armrest 40 is used, the person P to be examined lies with the top of his head situated substantially at one end of the tabletop 10 as shown in FIG. 4A. But when the headrest 30 is used, the person P lies with his head protruding beyond that end of the tabletop 10 as shown in FIG. 4B. However, the conventional tabletop 10 is supported at only one end and must be supported by the bed 20 along at least one end portion having a length x, irrespective of the position of the person to be examined on the tabletop. Therefore, the effective range of photographing varies whether the headrest is used and thus requires the person to be examined to lie with his head shifted on the tabletop.

In FIGS. 4A and 4B, a CT apparatus is shown as an example of a conventional photographing apparatus. The CT contains an X-ray tube (X) and a detector (D) that dictate a photographing position I. The oblique lines employed for a portion of the tabletop 10 in FIG. 4A or 4B denote where the attachment, such as headrest 30 or armrest 40, is connected to the tabletop 10. That portion defines a low-count region, since its connecting parts (such as the fixing pins 10c) are metallic and tend to produce a low-count artifact. The fact that the metallic parts narrow the effective range of photographing as mentioned impedes and inconveniences photographing.

What is required, as discovered by the present inventors is an attachment, such as a headrest or an armrest that does not impedes photographing or requires patients to be repositioned as extremities are photographed.

BRIEF SUMMARY OF THE INVENTION

It is an object of this invention to provide an image diagnosis bed apparatus and a bed attachment that (1) is easy to connect to or disconnect from the tabletop in the bed apparatus and (2) can be connected or installed in position without forming any low-count portion in the effective range of photographing.

According to a first aspect of this invention, the attachment has a connecting portion adapted for insertion in a connecting hole formed in the face of one end of the tabletop. The connecting portion has leaf springs for connecting it to the tabletop removably. Each spring has a protrusion engageable in a fixing hole formed in the surface of the tabletop on which the person to be examined may lie, and communicating with the connecting hole.

According to a second aspect of this invention, the attachment as a whole is formed from an X-ray transmitting material.

According to a third aspect of this invention, the attachment includes a headrest for supporting the head of the person to be examined, a footrest for supporting his legs, or a linking member for connecting either the headrest, the footrest or another supporting means for neither head nor foot support.

According to a fourth aspect of this invention, the attachment is shaped so as to be capable of being placed over a headrest connected to a tabletop in an image diagnosis bed apparatus.

According to a fifth aspect of this invention, the attachment includes an armrest with an opening for the insertion of the headrest at its bottom.

According to a sixth aspect of this invention, the headrest has a connecting portion adapted for insertion in a connecting hole formed in the face of one end of the tabletop in image diagnosis bed apparatus. The connecting portion has leaf springs for connecting it to the tabletop removably. Each spring has a protrusion engageable in a fixing hole formed in the surface of the tabletop on which the person to be examined may lie, and communicating with the connecting hole.

According to a seventh aspect of this invention, the attachment has a bottom having substantially the same shape with the surface of the tabletop on which the person to be examined may lie, so that they may fit each other.

According to an eighth aspect of this invention, there is an image diagnosis bed apparatus comprising a tabletop on which the person to be examined may lie, a bed for supporting the tabletop movably along the axis of the body of the person to be examined, a headrest connected to the tabletop removably for supporting the head of the person to be examined, and an attachment so shaped as to be placed over the headrest for supporting a part of the body of the person to be examined.

According to a ninth aspect of this invention, the tabletop and attachment of the bed apparatus as a whole are formed from an X-ray transmitting material.

BRIEF DESCRIPTION OF THE SEVERAL VIEWS OF THE DRAWING

The accompanying drawings illustrate various embodiments of the invention, and together with the general description given above and the detailed description of the preferred embodiments given below, serve to explain the principles of the invention.

DETAILED DESCRIPTION OF THE INVENTION

Figure 1:
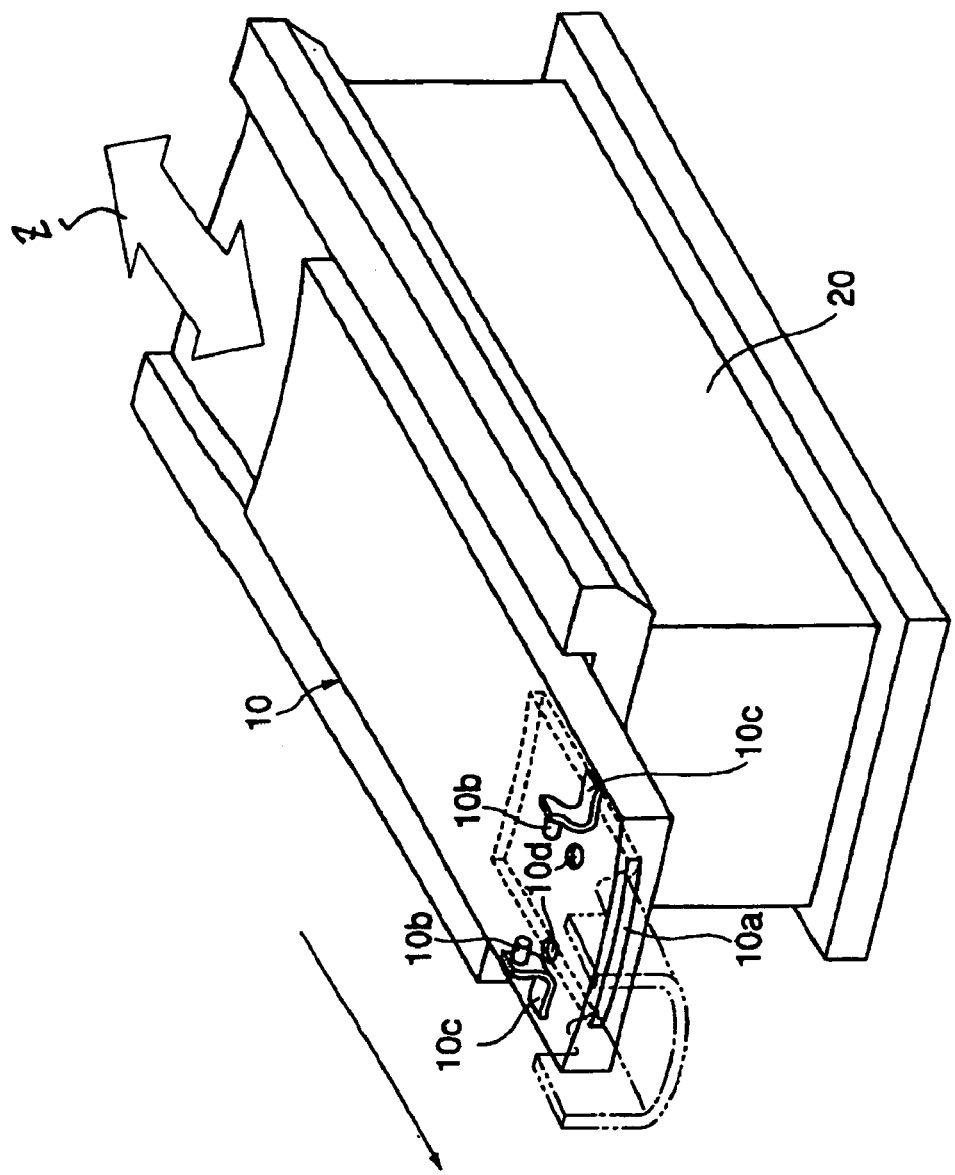
FIG. 1 is a view showing a conventional image diagnosis bed apparatus.
Figure 2:
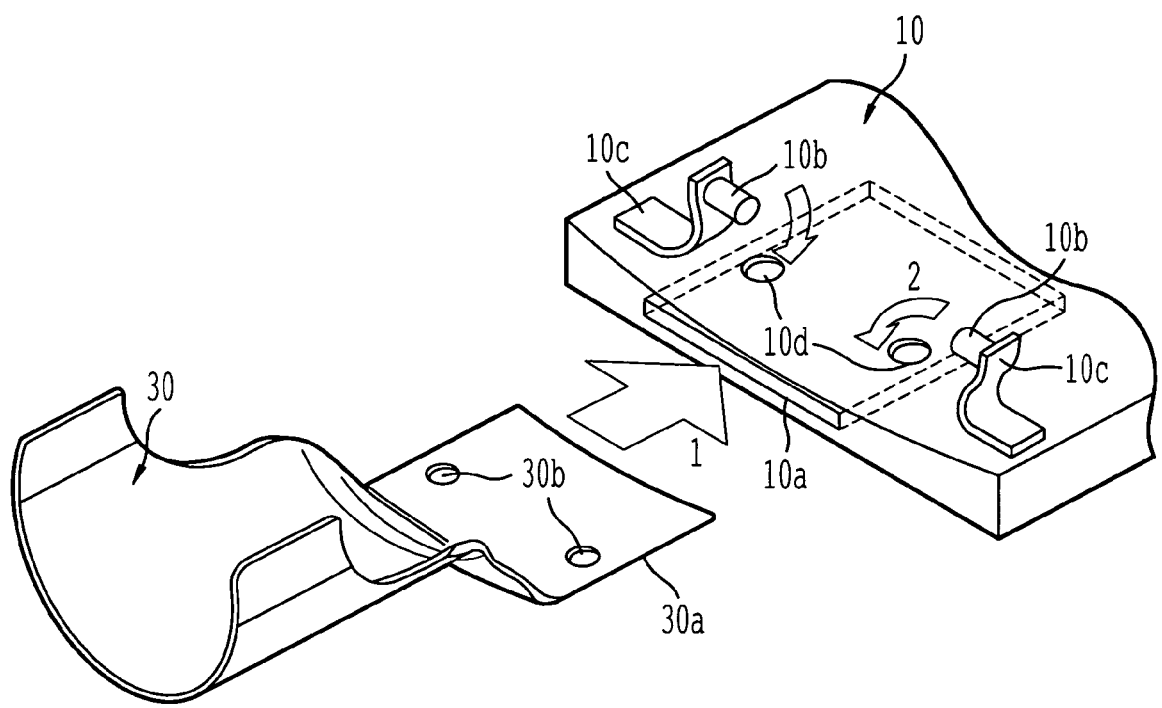
FIG. 2 is a view showing a process of connecting a convention headrest to the tabletop in the apparatus shown in FIG. 1.
Figure 3:
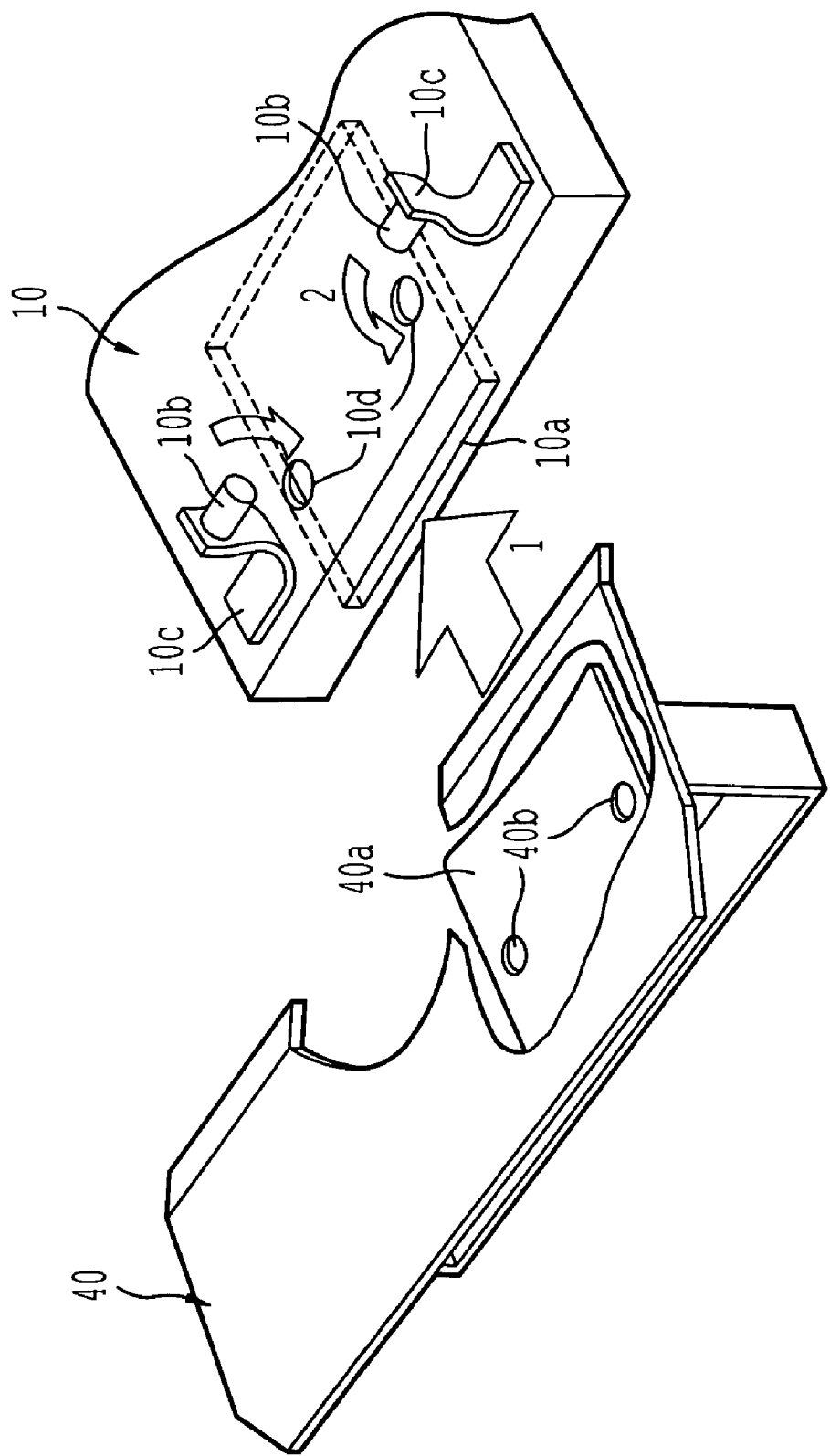
FIG. 3 is a view showing a process of connecting a conventional armrest to the tabletop in the apparatus shown in FIG. 1.
Figure 4A:
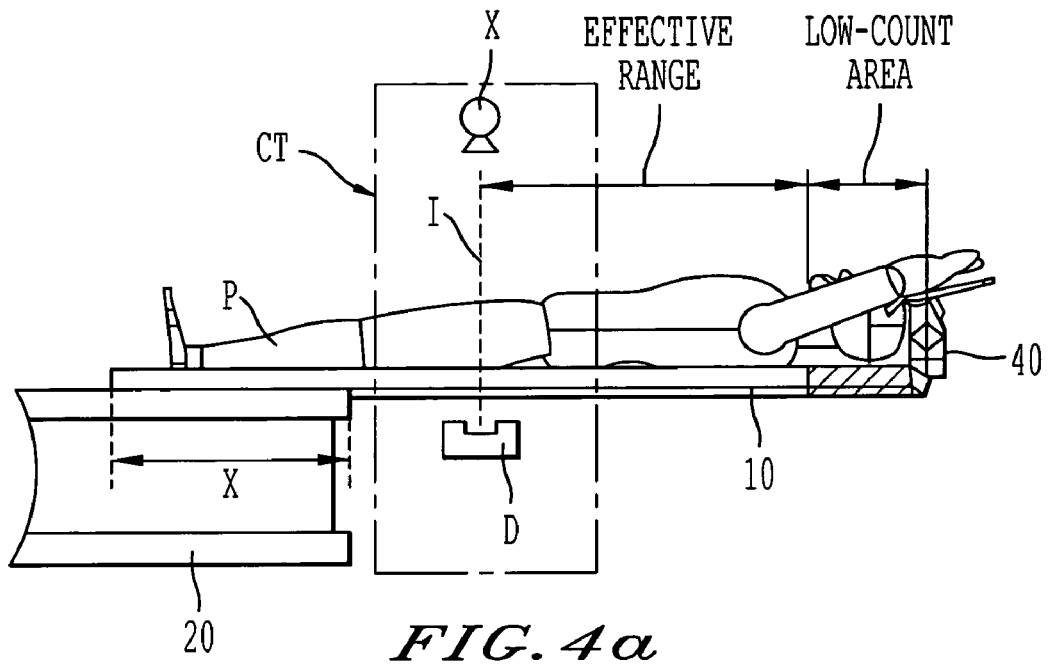
FIGS. 4A and 4B are views showing an effective range of photographing available in the apparatus shown in FIG. 1, respectively.
Figure 4B:
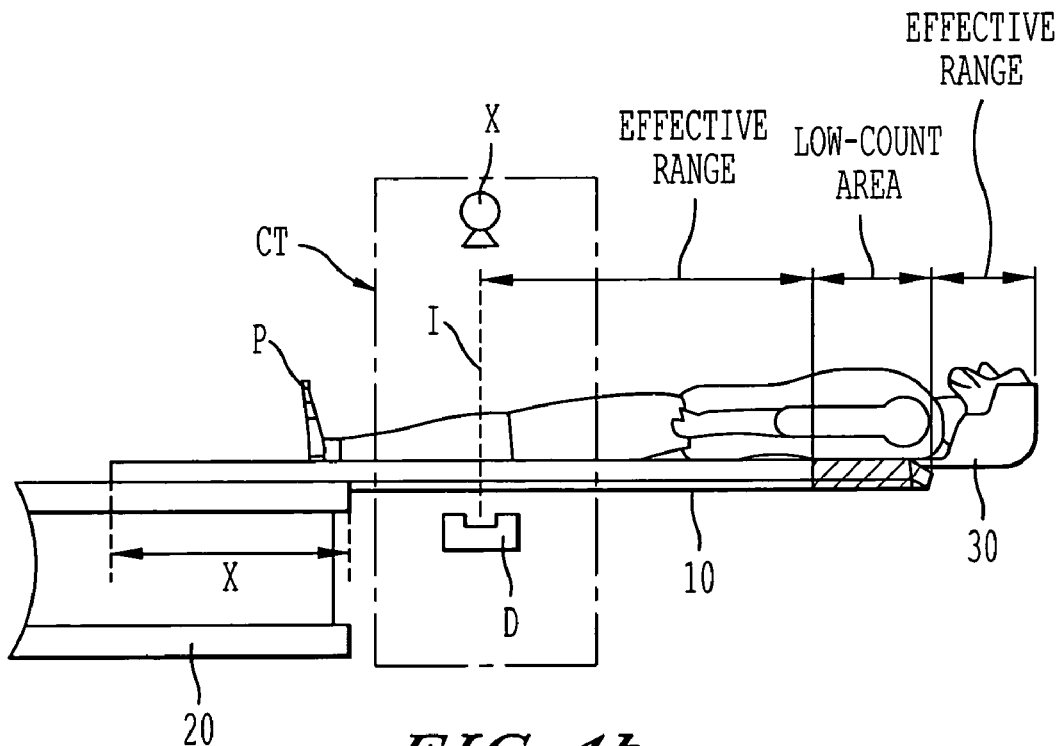
Figure 5:
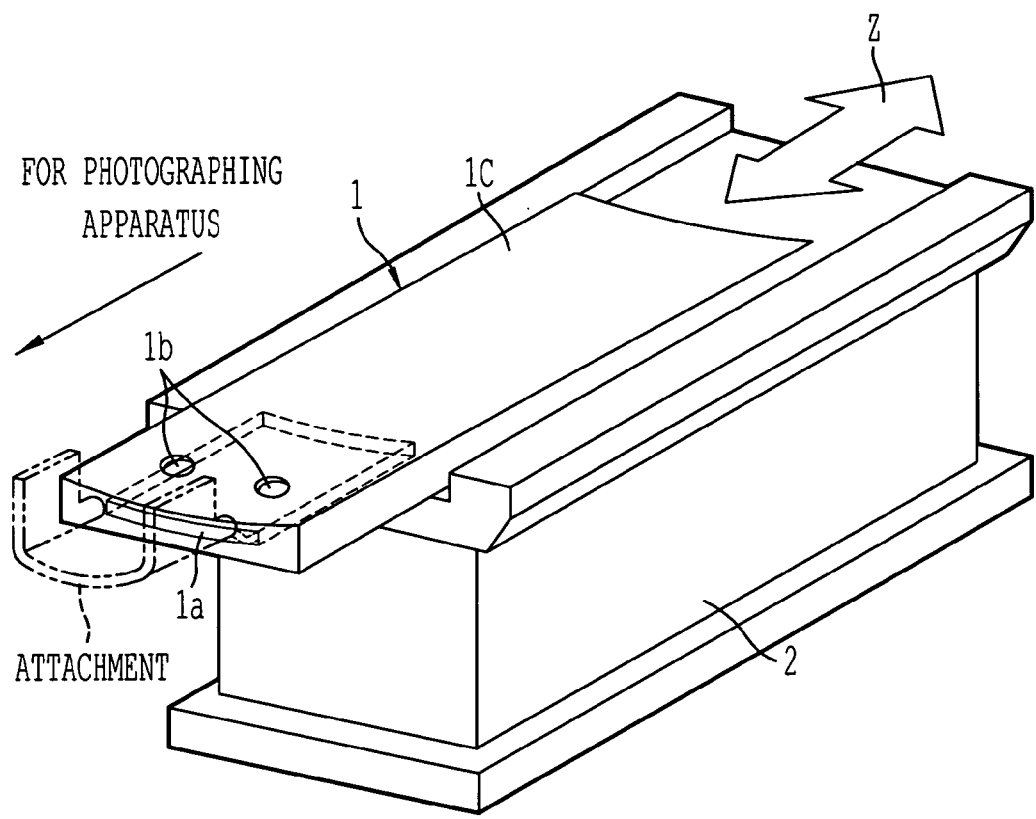
FIG. 5 is a view showing the whole of an image diagnosis bed apparatus to which an embodiment of the present invention may be fitted.

FIG. 5 is a view showing the whole structure of an image diagnosis bed apparatus to which one embodiment of this invention may be fitted. The apparatus has a tabletop 1 on which the person to be examined may lie and a bed 2 including a tabletop drive (not shown) for driving the tabletop 1. The tabletop 1 may be fitted with an attachment (shown by dotted lines in FIG. 5) such as a headrest, armrest, or footrest.

The tabletop 1 is so constructed as to be horizontally and reciprocally movable along the axis of the body of the person to be examined (along the arrow shown in FIG. 5) by the tabletop drive included in the bed 2 for conveying the person lying on the tabletop 1 into a photographing apparatus (e.g. a gantry for an X-ray CT apparatus).

The tabletop 1 has at its end facing the photographing apparatus a connecting hole 1a for connecting an attachment, such as a headrest, an armrest, or a footrest. At its top, the tabletop 1 has fixing holes 1b for fixing the attachment, such as a headrest, armrest, or footrest to the tabletop 1, and a concave surface 1c in which the person to be examined may lie. Accordingly, the attachment has a bottom having substantially the same shape with the top of the concave surface 1c, so that they may fit each other.

Figure 6:
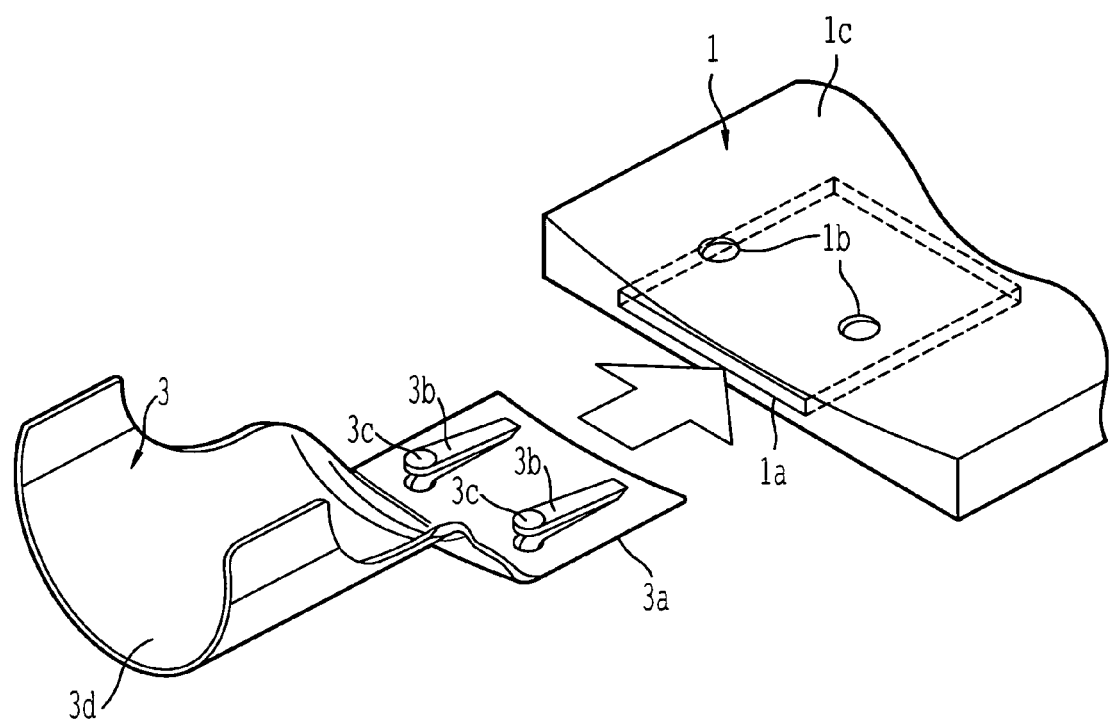
FIG. 6 is a view showing a process of connecting a headrest to the tabletop of the apparatus shown in FIG. 5.
Figure 7:
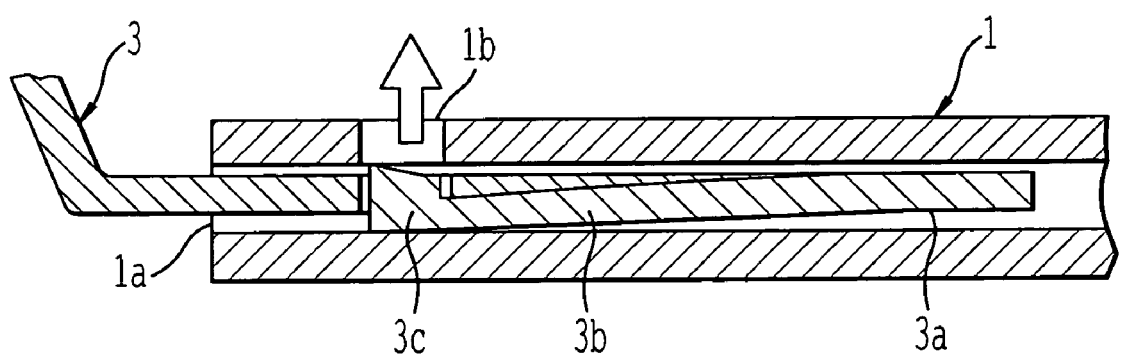
FIG. 7 is a view showing a process of fixing the headrest to the tabletop of the apparatus shown in FIG. 5.
Figure 8A:
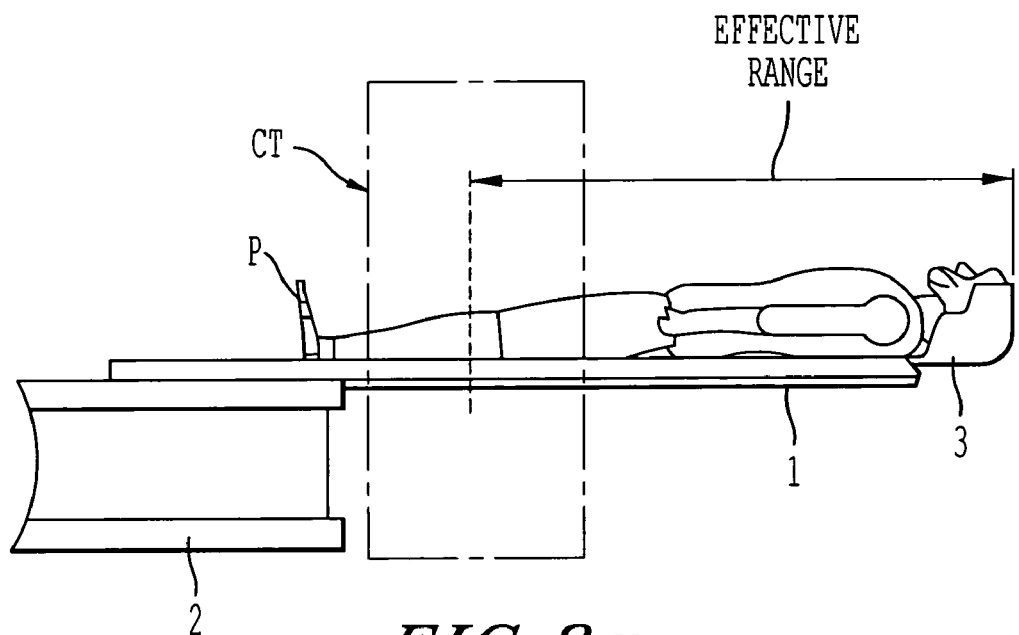
FIGS. 8A and 8B are views showing an effective range of photographing available in the image diagnosis bed apparatus to which an embodiment of the present invention is fitted, respectively.
Figure 8B:
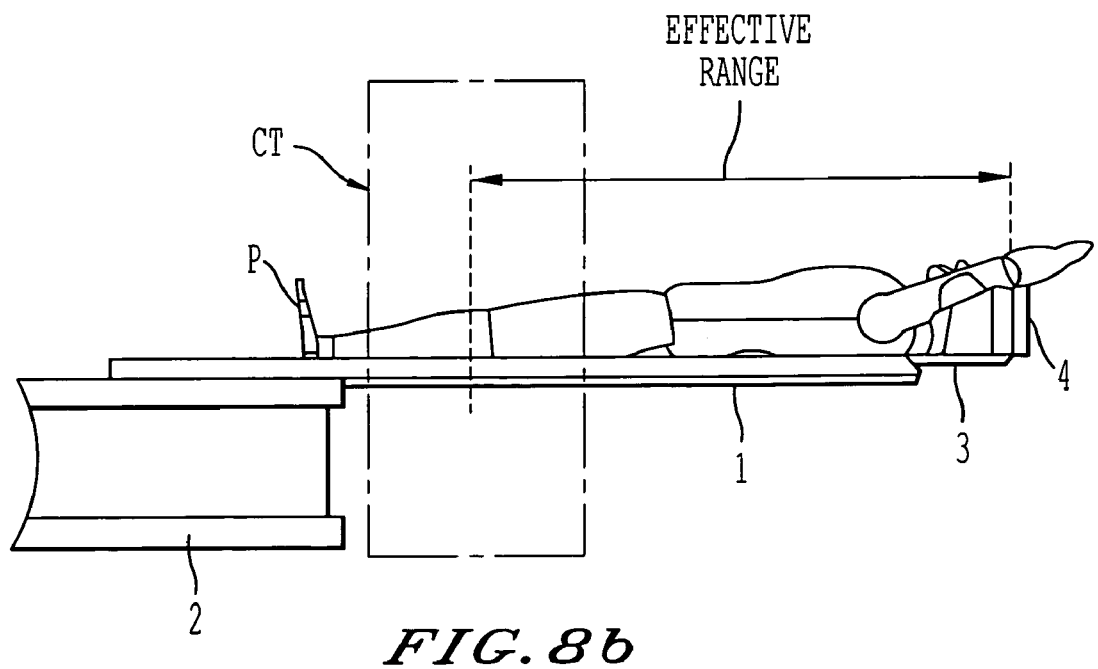

The headrest is a supporting device of small thickness for supporting the head of the person to be examined. The headrest is, as a whole, formed from an X-ray transmitting material, such as CFRP (Carbon Fiber Reinforced Plastics). The headrest 3 has a supporting portion 3d for supporting the head of the person to be examined, and a connecting portion 3a adapted for insertion in the tabletop 1, as shown in FIG. 6. The headrest can be connected with the tabletop 1 if its connecting portion 3a is inserted into the connecting hole 1a of the tabletop 1. The headrest 3 has leaf springs 3b in its connecting portion 3a and a protrusion 3c formed at the tip end of each spring, so that when the connecting portion 3a is connected into the connecting hole 1a, the protrusions 3c may fit in the fixing holes 1b, as shown in FIG. 7, to fix the headrest 3 to the tabletop 1. The headrest 3 is removable from the tabletop 1 if it is pulled out with its protrusions 3c held down.

In one embodiment, the leaf springs 3b and protrusions 3c may be formed in the tabletop 1, as the tabletop 1 is of the hollow construction. In such a case, the fixing holes 1b may be formed in the headrest 3. It is, however, preferable to form the leaf springs 3b and protrusions 3c integrally with the headrest 3, since they are easier to form on the headrest 3 than on the tabletop 1.

When the headrest 3 is connected to the tabletop 1, no low-count region is formed in the vicinity of the end of the tabletop since the headrest 3 as a whole is formed from an X-ray transmitting material. Therefore, a large region and range of motion having no loss is available.

The use of the leaf springs for fixing the headrest to the tabletop simplifies and facilitates the work of connecting the headrest to the tabletop and removing it. The headrest formed as a whole from an X-ray transmitting material eliminates any loss in the range of photographing.

Figure 9:
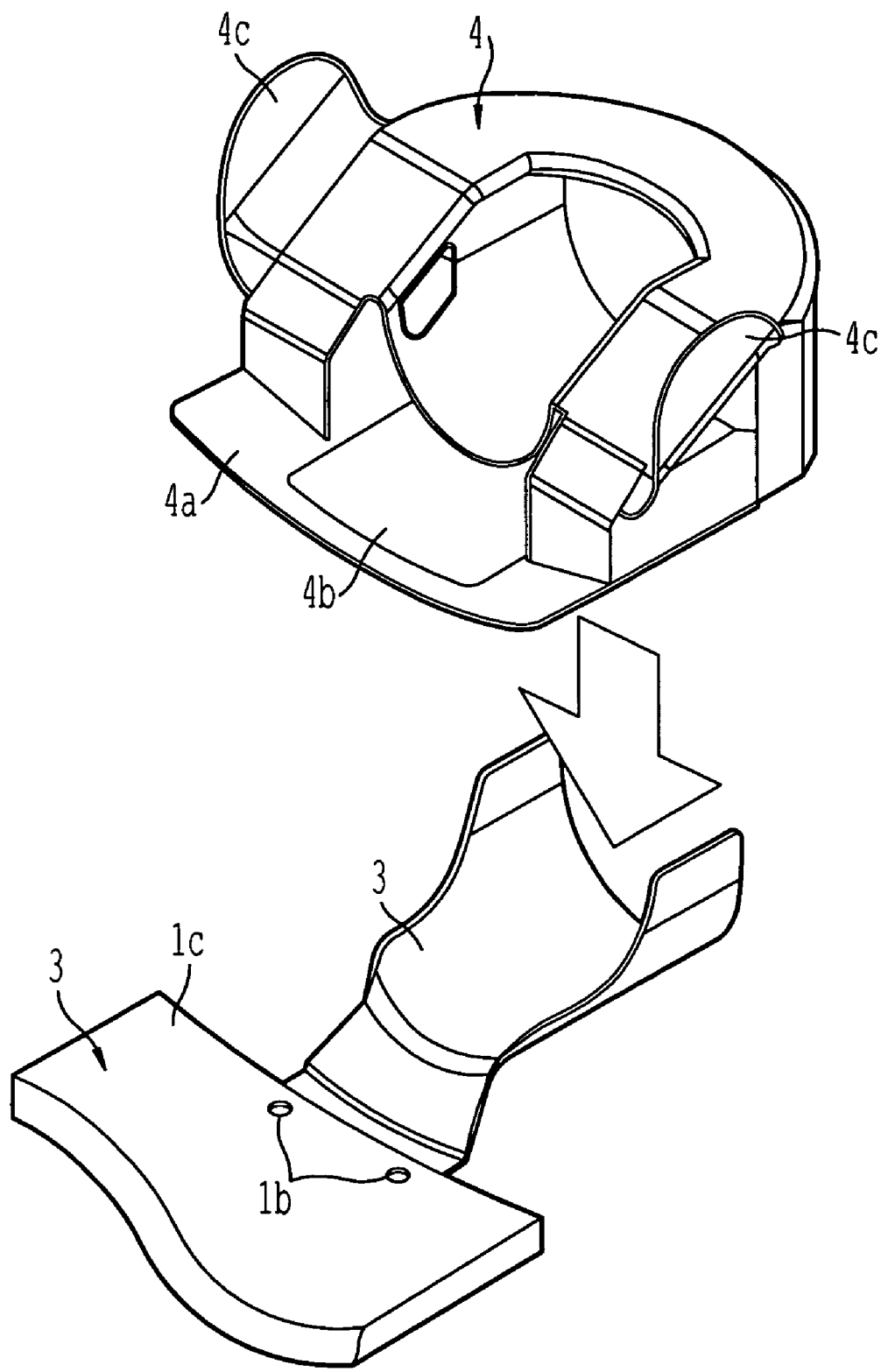
FIG. 9 is a view showing a process of placing an armrest over a headrest in one embodiment of the present invention.
Figure 10:
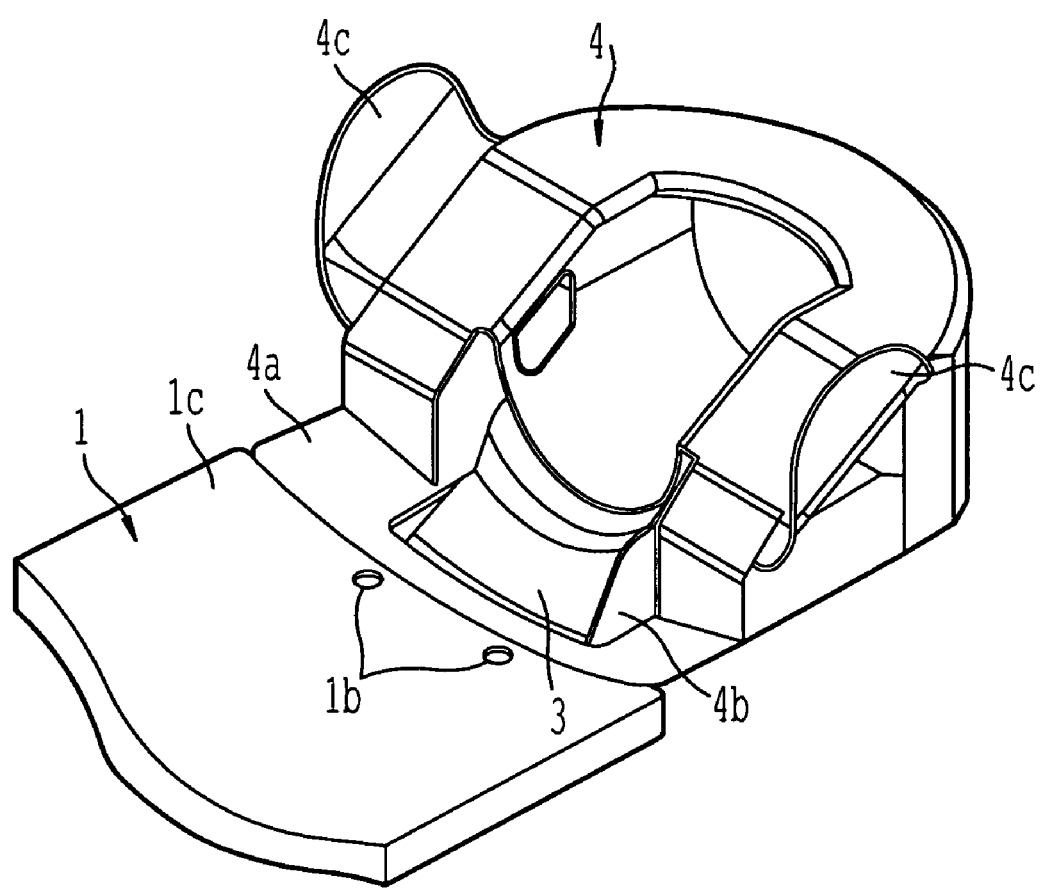
FIG. 10 is a view showing the armrest placed over the headrest in one embodiment of the present invention.
Figure 11:
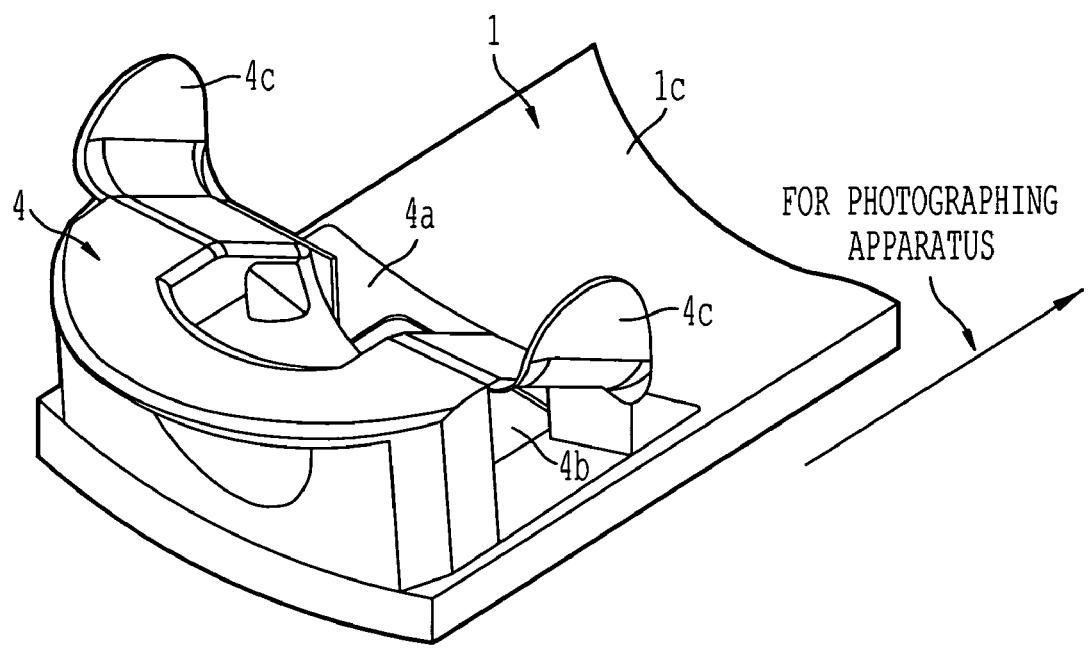
FIG. 11 is a view showing the armrest placed on the tabletop in one embodiment of the present invention.

Description will now be made of an armrest embodying this invention with reference to FIGS. 9 to 11. The armrest is used for supporting the upper arm portions of the person to be examined in the vicinity of his head so that his arms may not obstruct the photographing of the upper half of his body. The armrest as a whole is formed from an X-ray transmitting material, such as CFRP. Alternatively, the armrest 4 can be formed from X-ray absorption material (e.g. metallic) if the upper region above the chin is not included in the photographing area. The armrest 4 has an insertion opening 4b in its bottom plate 4a, as shown in FIG. 9. Therefore, the armrest 4 can be placed over the headrest 3 if the insertion opening 4b is fitted over the headrest 3. The headrest 3 serves to fix the armrest 4 in position. FIG. 10 shows the headrest and armrest together. The armrest 4 has two support guides 4c formed along two edges thereof, respectively, for supporting the upper arm portions of the person to be examined. The bottom plate 4a has a convex surface fitting the concave top surface 1c of the tabletop 1, so that the armrest 4 can be placed directly on the top of the tabletop 1, as shown in FIG. 11. Therefore, it is possible to carry out the foot-fast photographing of a person lying in the opposite direction (with his head held remote from a photographing apparatus) if the armrest 4 is placed on the tabletop 1 at its end remote from the photographing apparatus, as shown in FIG. 11.

When the armrest 4 is placed on or fixed to the headrest 3, no low-count region is formed in the vicinity of the end of the tabletop since the armrest 4 as a whole is formed from an X-ray transmitting material. Therefore, a large region and range of motion having no loss is available. The arms of the person P to be examined are, however, lowered for the photographing of his head.

That armrest can be placed over the headrest for securing to the tabletop eliminates the necessity of removing the headrest from the tabletop prior to the use of the armrest and thereby facilitates the setting in position of the person to be examined. The use of the armrest does not require any movement of the person to be examined, or any reduction in the range of photographing available. The armrest formed as a whole from an X-ray transmitting material eliminates any loss in the range of photographing. Moreover, the armrest that can be placed directly on the tabletop makes foot-fast photographing possible if it is placed on the tabletop at its end remote from the photographing apparatus.

Figure 12:
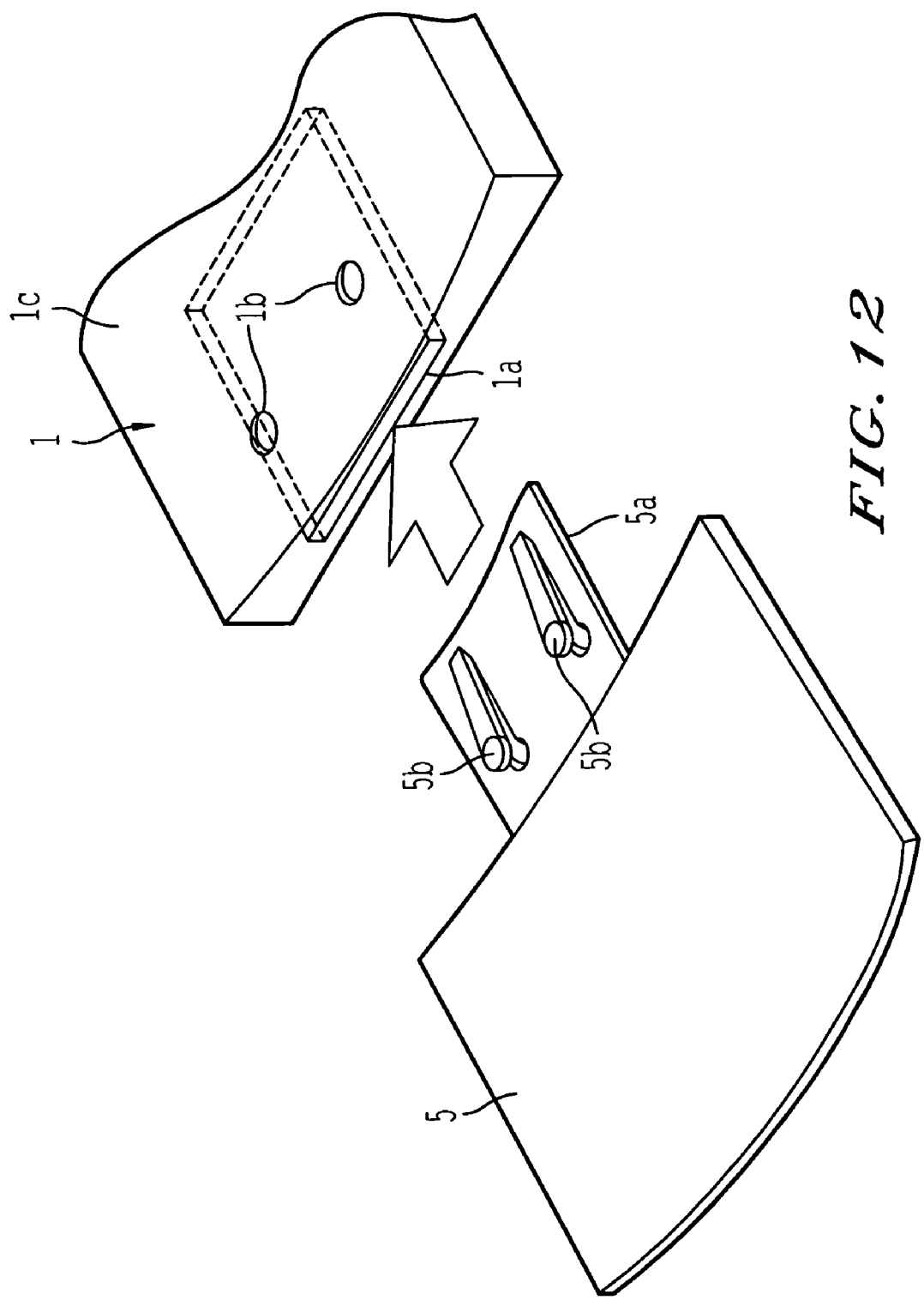
FIG. 12 is a view showing a process for connecting a footrest to the tabletop of the apparatus shown in FIG. 5.

Description will now be made of a footrest embodying this invention with reference to FIG. 12. The footrest is used for supporting the legs of the person to be examined on the occasion of foot-fast photographing. Although foot-fast photographing may, of course, be possible without the aid of any footrest, the use of a footrest enables the person lying to be examined to be shifted toward his legs, and thereby makes available a correspondingly enlarged effective range of photographing. Thus, a footrest is often used for foot-fast photographing.

The footrest is similar in construction to the headrest as described before, except its shape. Thus, as a whole it is formed from an X-ray transmitting material, such as CFRP. It can be connected to the tabletop 1 if its connecting portion 5a is inserted into the connecting hole 1a of the tabletop 1, as shown in FIG. 12. The footrest 5 has leaf springs 5b on its connecting portion 5a so that when the connecting portion 5a is connected into the connecting hole 1a, the leaf springs 5b may fit in the fixing holes 1b to fix the footrest to the tabletop 1. The footrest 5 is removable from the tabletop 1 if it is pulled out with its leaf springs 5b held down.

The leaf springs 5b may alternatively be formed in the tabletop 1, as the tabletop 1 is of the hollow construction. In such a case, the fixing holes 1b may be formed in the footrest 5. It is, however, preferable to form the leaf springs 5b integrally with the footrest 5, since they are easier to form on the footrest 5 than on the tabletop 1.

The use of the leaf springs for fixing the footrest to the tabletop simplifies and facilitates the work of connecting the footrest to the tabletop and removing it. The footrest formed as a whole from an X-ray transmitting material eliminates any loss in the range of photographing.

Figure 13:
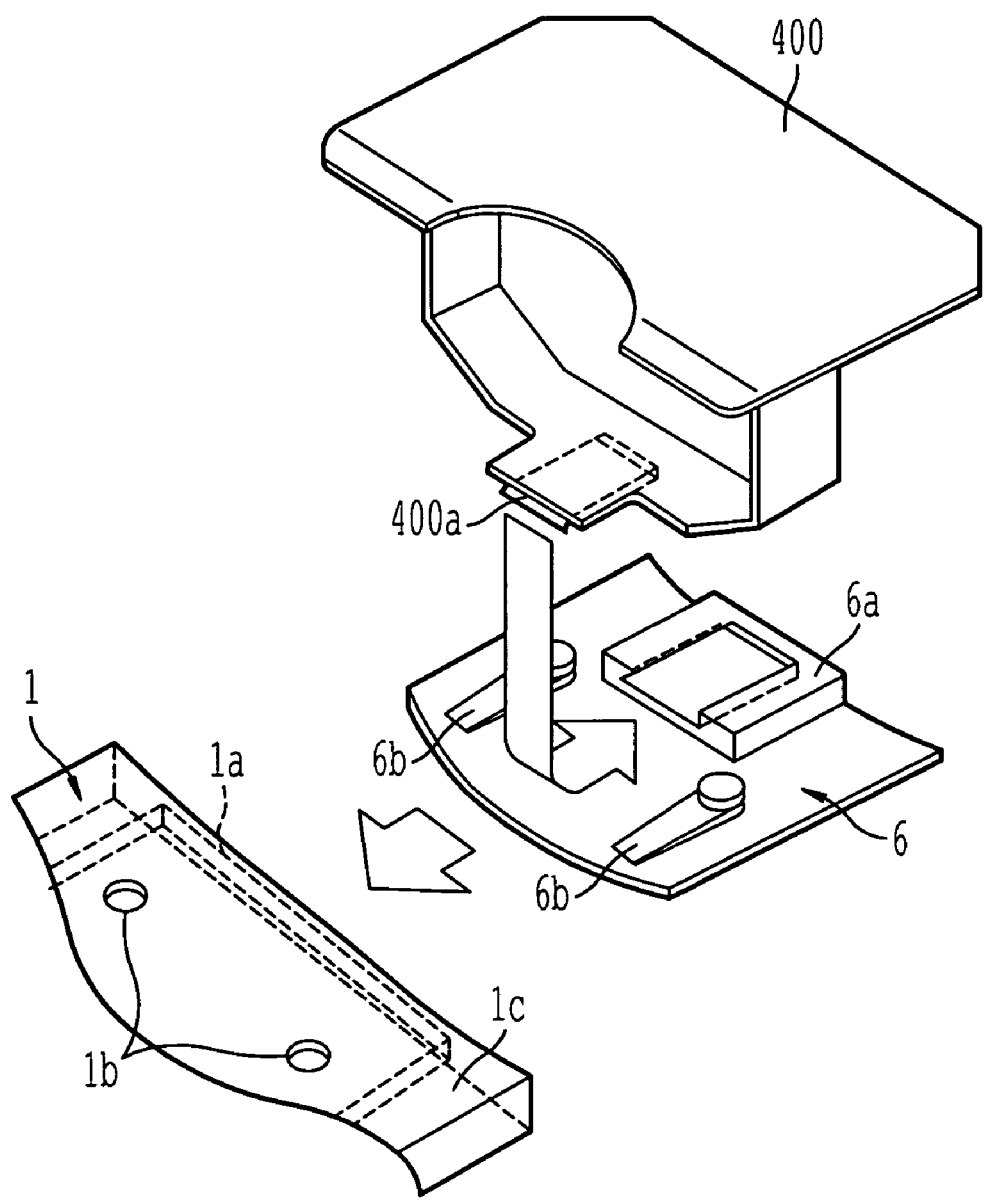
FIG. 13 is a view showing a process of connecting a conventional armrest to the tabletop of the present invention by way of a linking member.

An image diagnosis bed apparatus according to this invention may be so constructed as to permit the use of an attachment used normally for a different bed apparatus (e.g. an armrest 400 as shown in FIG. 13) with the aid of a linking device 6 as shown in FIG. 13. The linking device 6 is as a base portion formed from an X-ray transmitting material, and is basically similar in construction to the headrest 3, or footrest 5 as described before, except its connecting portion 6a that will now be described. Here, the connecting portion 6a can be formed from metallic material.

The armrest 400 has a trapezoidal connecting portion 400a as shown in FIG. 13, and can be connected to the tabletop not shown if its connecting portion 400a is inserted into the connecting hole of the tabletop. The linking device 6 has a correspondingly concavely shaped connecting portion 6a to which the armrest 400 can be connected. The linking device 6 also has leaf springs 6b for connecting or fixing the linking device 6 to the tabletop 1, and can be connected or fixed to the tabletop if it is inserted into the connecting hole 1a of the tabletop 1. The linking device 6 is removable from the tabletop 1 if it is pulled out with its leaf springs 6b held down.

The leaf springs 6b may alternatively be formed in the tabletop 1, as the tabletop 1 is of the hollow construction. In such a case, the fixing holes 1b may be formed in the linking device 6. It is, however, preferable to form the leaf springs 6b integrally with the linking device 6, since they are easier to form on the linking device 6 than on the tabletop 1.

Thus, any attachment used normally for a different bed apparatus for image diagnosis can be used with previously described embodiments of this invention with the aid of a linking device having a connecting portion fitting any such attachment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus, comprising:
a tabletop of an image diagnosis bed having a surface with a fixing hole and a connecting hole formed in a face of one end of the tabletop; and
a headrest for supporting the head of a person, the headrest including a connecting portion adapted for insertion in the connecting hole and having leaf springs configured to connect the headrest to the tabletop removably, each leaf spring having a protrusion engageable in the fixing hole and configured to communicate with the connecting hole, wherein the headrest and the connecting portion are made of an X-ray transmitting material, and
wherein the headrest is configured to attach to an armrest including an armrest bottom and an armrest opening configured for insertion onto the headrest, the armrest including two support guides formed along two edges of the armrest and configured to support upper arm portions of the person, and a bottom plate that fits a top surface of the tabletop.

2. The X-ray CT apparatus of claim 1, wherein the bottom plate of the armrest is formed below the two support guides.

3. The X-ray CT apparatus of claim 1, wherein the bottom plate of the armrest has a convex surface fitting the top surface of the tabletop, the top surface of the table top being a concave surface.

4. An X-ray CT apparatus, comprising:
a tabletop of an image diagnosis bed, the tabletop having a surface with a fixing hole and a connecting hole formed in a face of one end of the tabletop;
a headrest configured to support a head of a person and to connect the headrest to the tabletop removably; and
an armrest configured to be placed over and substantially cover the headrest and having two support guides formed along two edges of the armrest and configured to support upper arm portions of the person,
wherein the armrest is configured to be removed while the headrest is connected to the tabletop, the armrest includes a bottom plate that fits a top surface of the tabletop, and the armrest is made of an X-ray transmitting material.

5. The apparatus according to claim 4, wherein the tabletop and headrest, each comprise:
an X-ray transmitting material.

6. The apparatus according to claim 4, wherein the armrest comprises a bottom portion and an opening portion configured for insertion onto the headrest.

7. The X-ray CT apparatus of claim 4, wherein the bottom plate of the armrest is formed below the two support guides.

8. The X-ray CT apparatus of claim 4, wherein the bottom plate of the armrest has a convex surface fitting the top surface of the tabletop, the top surface of the table top being a concave surface.

* * * * *